US009988682B2

(12) United States Patent
Hall

(10) Patent No.: US 9,988,682 B2
(45) Date of Patent: Jun. 5, 2018

(54) METHOD FOR MEASURING BONE LOSS RATE

(71) Applicant: Nobel Biocare Services AG, Kloten (CH)

(72) Inventor: Jan Hall, Gothenburg (SE)

(73) Assignee: Nobel Biocare Services AG, Kloten (CH)

(*) Notice: Subject to any disclaimer, the term of this patent is extended or adjusted under 35 U.S.C. 154(b) by 302 days.

(21) Appl. No.: 14/765,782

(22) PCT Filed: Feb. 7, 2014

(86) PCT No.: PCT/EP2014/052463
§ 371 (c)(1),
(2) Date: Aug. 4, 2015

(87) PCT Pub. No.: WO2014/122279
PCT Pub. Date: Aug. 14, 2014

(65) Prior Publication Data
US 2015/0368716 A1 Dec. 24, 2015

(30) Foreign Application Priority Data
Feb. 8, 2013 (GB) .................................. 1302257.9

(51) Int. Cl.
*C12Q 1/68* (2018.01)
(52) U.S. Cl.
CPC ...... *C12Q 1/6883* (2013.01); *C12Q 2600/112* (2013.01); *C12Q 2600/158* (2013.01)
(58) Field of Classification Search
None
See application file for complete search history.

(56) References Cited

U.S. PATENT DOCUMENTS

| 6,143,506 A | 11/2000 | Golub et al. | |
|---|---|---|---|
| 2004/0023207 A1* | 2/2004 | Polansky | A61K 31/00 435/5 |
| 2007/0105101 A1* | 5/2007 | Susa Spring | C12Q 1/6813 435/6.13 |
| 2011/0105349 A1 | 5/2011 | Houston et al. | |
| 2011/0189186 A1* | 8/2011 | Feng | C07K 16/2896 424/138.1 |
| 2013/0022501 A1* | 1/2013 | Fine | G01N 33/6863 422/82.08 |

FOREIGN PATENT DOCUMENTS

| EP | 0 974 671 A1 | 1/2000 |
|---|---|---|
| WO | WO 95/12124 A1 | 5/1995 |
| WO | WO 00/13024 A1 | 3/2000 |
| WO | WO 02/077639 A2 | 10/2002 |
| WO | WO 2009/053091 A2 | 4/2009 |
| WO | WO 2009/127855 A1 | 10/2009 |

OTHER PUBLICATIONS

Hall et al. A controlled clinical exploratory study on genetic markers for peri-implantitis. Eur J Oral Implantol 4(4):371-382 (2011).*
Moffet & Moore. The Standard of Care: Legal History and Definitions: the Bad and Good News. Western Journal of Emergency Medicine. vol. 12, No. 1, Feb. 2011. (Year: 2011).*
Ahlqvist, J. et al., "Osseointegrated Implants in Edentulous Jaws: A 2-year Longitudinal Study," Int J. Oral Maxillofac Implants, vol. 5, 1990, 155-163.
Beck Jensen, J.E. et al., "A single measurement of biochemical markers of bone turnover has limited utility in the individual person," Scand. J. Clin. Lab. Invest., vol. 57, 1997, pp. 351-360.
Bustin, S.A., "The MIQE Guidelines: Minimum Information for Publication of Quantitative Real-Time PCR Experiments," Clinical Chemistry, vol. 55, No. 4, 2009, pp. 611-622.
Christenson, R.H., "Biochemical markers of bone metabolism: an overview," Clinical Biochemistry, vol. 30, No. 8, Dec. 1997, pp. 573-593.
Cochran, D.L., "Inflammation and Bone Loss in Periodontal Disease," J. Periodontol, vol. 79, Aug. 2008, pp. 1569-1576.
Duarte, P.M. et al., "Differential cytokine expressions affect the severity of peri-implant disease" Clin. Oral Impl. Res., vol. 20, 2009, pp. 514-520.
Janckila, a.J. et al., "Stable expression of human tartrate-resistant acid phosphates isoforms by CHO cells," Clin, Chimica Acta, vol. 326, 2002, pp. 113-122.
Keiler, A.M. et al., "Estimation of an early meaningful time point of bone parameter changes in application to an osteoporotic rat model with in vivo microcomputed tomography measurements", Lab. Animals, vol. 46, 2012, pp. 237-244.
Misch, C.E. et al., "Implant Success, Survival, and Failure: The International Congress of Oral Implantologists (ICOI) Pisa Consensus Conference," Implant Dentistry, vol. 17, No. 1, 2008, pp. 5-15.
Mogi, M. and Otogoto J., "Expression of cathepsin-K in gingival crevicular fluid of patients with periodontitis," Arch Oral Biol. vol. 52, 2007, pp. 894-898.
Seibel, M.J., "Biochemical Markers of Bone Turnover. Part I: Biochemistry and variability" Clin Biochem Rev, vol. 26, Nov. 2005, pp. 97-122.
Slotte, C. et al., "Gene expression of inflammation and bone healing in peri-implant crevicular fluid after placement and loading of dental implants. A kinetic clinical pilot study using quantitative real-time PCR," Clin. Implant Dentistry Rel. Res., vol. 14, No. 5, 2012, pp. 723-736.

(Continued)

*Primary Examiner* — Samuel C Woolwine
(74) *Attorney, Agent, or Firm* — Knobbe, Martens, Olson & Bear LLP

(57) ABSTRACT

The present invention relates to a method for diagnosing bone loss rate, particularly in the field of bone anchored implants. The present patent provides with a method that comprises the steps of: a) quantifying the expression level of one or more markers or ratio thereof related to the activity of osteoclasts and/or osteoblasts in an ex vivo sample; and b) determining the bone loss rate as a function of ongoing loss of marginal bone level by interpolating the value obtained in step a) in one or more calibration curves. The invention also relates to a kit for performing said method.

9 Claims, 2 Drawing Sheets

(56) References Cited

OTHER PUBLICATIONS

Stepan, J.J. et al., "Markers of bone remodeling predict rate of bone loss in multiple sclerosis patients treated with low dose glucocorticoids" Clinica Chimica Acta, vol. 348, 2004, pp. 147-154.

Strbac, G.D. et al., "Cathepsin K levels in the crevicular fluid of dental implants: a pilot study" J. Clinical Periodontology, vol. 33, 2006, pp. 302-308.

International Search Report for Application No. PCT/EP2014/052463 dated Apr. 3, 2014 in 6 pages [the ISR for the PCT Application of this US national phase application].

* cited by examiner

METHOD FOR MEASURING BONE LOSS RATE

CROSS-REFERENCE TO RELATED APPLICATIONS

This application is a national stage application under 35 U.S.C. § 371 of International Application No. PCT/EP2014/052463, filed on Feb. 7, 2014, which published in English as WO 2014/122279 A1 on Aug. 14, 2014 and which claims priority benefit of GB Patent Application No. 1302257.9 filed on Feb. 8, 2013.

TECHNICAL FIELD

The present invention relates to a method for diagnosing bone loss rate, particularly in the field of bone anchored implants.

BACKGROUND ART

A large number of dental implant rehabilitation procedures are performed every year. In contrast to the vast majority of cases where implant treatment is successful, a certain number of patients develop peri-implant disease (PI). In some cases, non-surgical treatment with mechanical debridement and flushing with 3% hydrogen peroxide may be a sufficiently effective treatment. In cases of persisting peri-implant disease, resective surgery in combination with surface debridement is often performed. By surgical correction of osseous defects (e.g. bone peaks) at the diseased implant site, pocket depths can be reduced and provide for a soft tissue morphology that facilitates oral hygiene. However, certain patients do not respond sufficiently well to treatment, and in spite of good plaque control and minimal inflammation of the peri-implant mucosa, symptoms including suppuration and progressive bone loss may recur in some cases. The reasons for such relapses are not known. A desire for improved understanding of the etiology of peri-implant disease and for the development of more sensitive diagnostic tools allowing for earlier detection and interventions is at hand; thus, increasing the predictability of implant treatment in susceptible patients. Moreover, in order to increase the survival rate of implants presenting signs of bone loss, clinical intervention at an early stage of disease progression is desirable. This requires early establishment of possible ongoing bone resorption, and therefore, more sensitive techniques are required.

Bone resorption is mediated by bone resorption cells, osteoclasts, which are formed by mononuclear phagocytic cells. New bone replacing the lost bone is deposited by bone-forming cells, osteoblasts, which are formed by mesenchymal stromal cells. Various other cell types that participate in the remodeling process are tightly controlled by systemic factors (e.g., hormones, lymphokines, growth factors and vitamins) and local factors (e.g., cytokines, adhesion molecules, lymphokines and growth factors) (WO2012/061907).

The diagnosis of peri-implant disease is generally based on clinical measurements combined with radiographic evidence of bone loss. Peri-implantitis is often clinically translated into formation and deepening of pockets, breakdown of the peri-implant epithelial seal, bleeding on probing (BoP), purulence and progressive bone loss. These diagnostic methods are often used in combination for diagnosis of peri-implant disease as indicators of extensive pathologic changes in the implant-supporting tissue. The limited sensitivity and/or specificity of such diagnostic methods make early detection of pathologic changes difficult.

The viability of using analysis of genetic markers in the gingival crevicular fluid in plaque samples as a potential prognostic and diagnostic tool for peri-implant disease has been studied by a number of authors with variable results.

An often studied marker is Interleukin-1β (IL-1β), which is a pro-inflammatory cytokine involved in several biologic processes, including immune regulation, inflammation and connective tissue metabolism. IL-1β stimulates bone resorption and inhibits bone formation (Panagakos et al., Int J Oral Maxillofac Implants 1996, 11:794-799). IL-1β is produced mainly by macrophages but also by other cells including neutrophilic granulocytes. Several studies have shown the presence of IL-1β in the crevicular fluid around implants presenting signs of peri-implant disease. Significantly elevated levels have been reported for peri-implantitis compared to healthy sites (Panagakos et al., Int J Oral Maxillofac Implants 1996, 11:794-799; Kao et al., Int J Oral Maxillofac Implants 1995, 10:696-701; Murata et al., Clin Oral Impl Res 2002, 13:637-643) and compared to peri-implant mucositis sites (Murata et al., Clin Oral Impl Res 2002, 13:637-643), and also when comparing subjects with early and advanced signs of peri-implantitis. However, Hultin et al. (Clin Oral Impl Res 2002, 13:349-358) showed contradictory results with no difference in IL-1β expression between peri-implantitis and healthy sites.

Interleukin-8 (IL-8) is a proinflammatory marker and chemotactic factor for neutrophils. It participates in the regulation of the innate immune response to microbial invasion in periodontitis (Nassar et al., Infection and Immunity 2002, 268-276; Goutoudi et al., Int J Dent 2012; 2012:362905) and peri-implantitis (Petkovic et al., Int J Oral Maxillofac Surg 2010, 39(5):478-85). Nowzari et al. (Clin Implant Dent Relat Res 2008, 10(3):166-173) studied cytokine presence around implants and teeth in healthy subjects, and found a two-fold increase of IL-8 around implants compared with teeth.

Interleukin-6 (IL-6) is a multifunctional cytokine produced by various cells to regulate hematopoiesis, inflammation, immune responses, and bone homeostasis (Yoshitake et al., J Biol Chem 2008, 283:11535-11540). The level of IL-6 in saliva samples from subjects with peri-implant disease was significantly elevated compared with saliva samples from healthy subjects in a study by Liskmann et al. (Int J Oral Maxillofac Implants 2006, 21(4):543-50). Konttinen et al (Int J Periodontics restorative Dent 2006, 26:135-141) measured statistically higher levels of IL-6 at failing implants with peri-implantitis compared with healthy implant sites.

Osteoclasts are bone resorbing cells originating from progenitor cells of the monocyte/macrophage lineage. The process of osteoclastogenesis is coordinated by receptor activator of NF-κB ligand (RANKL) and osteoprotegerin (OPG), which are members of the tumor necrosis factor super family. While RANKL induces osteoclastogenesis, its antagonist OPG inhibits the formation of osteoclasts (Boyle et al., Nature 2003, 423:337-342; Leibbrandt et al., Ann NY Acad Sci 2008, 1143:123-150). OPG has also been found to decrease osteoclast apoptosis (Chamoux et al., J Cell Physiol. 2008, 216(2):536-42). RANKL and OPG are secreted by osteoblasts, fibroblasts and endothelial cells (Corralini et al., J Cell Physiol. 2011, 226(9):2279-2286). RANKL is also expressed by activated T cells (Saidenberg-Kermanac'h et al., Eur Cytokine Netw. 2002, 13(2):144-53). It has been suggested that an imbalance in the equilibrium between OPG and RANKL may be related to diseases involving bone destruction such as periodontitis. For example, Bostanci et al., (J Clin Periodontol 2007, 34:370-376) showed that RANKL and OPG levels in the gingival crevicular fluid were oppositely regulated in periodontitis but not in gingivitis; hence, a significantly lower RANKUOPG ratio was recorded in gingival crevicular fluid around healthy teeth compared to teeth presenting various degrees of periodontal disease. Nevertheless, two studies of OPG and soluble RANKL in crevicular fluid around implants have failed to show statistically significant correlations with clinical parameters (Arikan et al., Clin Oral Impl Res 2008, 19:283-288; Monov et al., Clin Implant Dent Relat Res 2006, 8(3):135-141). However, in both studies numerous samples were outside the detection limit of the assay and either were excluded from the statistical calculations or accounted as 0. Hence, the authors conclude that the presented data should be interpreted with regard to these limitations. The role of OPG for the pathogenesis of arthritis has also been studied. For example, Liu et al. (Chin Med J (Engl). 2010, 123(11):1407-12) reported that the level of circulating OPG was elevated in subjects with early rheumatoid arthritis. It has been shown that Wnt proteins can promote maintenance and proliferation of stem cells (Willert et al., Nature 2003, 423(6938):448-52), and Wnt signaling plays a dominant role for osteoblastogenesis (for review, see Yavropoulou et al., Hormones, 2007, 6(4):279-294).

Cathepsin K (CatK) is a bone resorption marker, which is highly expressed in active osteoclasts. Higher CatK expression in peri-implantitis sites compared to healthy sites has been demonstrated (Strbac et al., J Clin Periodontol 2006; 33:302-308).

Osteocalcin (OC) is a calcium-binding protein of bone involved in bone mineralization and calcium homeostasis. Murata et al. (Clin Oral Impl Res 2002, 13:637-643) showed increases in OC expression in peri-implant crevicular fluid (PICF) from mucositis sites compared to healthy sites, while no differences in OC levels were seen between peri-implantitis sites and mucositis or healthy implant sites.

Matrix metalloproteinases (MMPs) are proteolytic enzymes involved in degradation and removal of collagen from damaged tissue. MMPs are secreted by cells residing in the inflammatory sites in response to stimuli such as lipopolysaccharide and cytokines (Aboyoussef et al., Int J Oral Maxillofac Implants 1998, 13:689-696). Collagenases and gelatinases are two sub-families of the MMP superfamily. Findings by Kivelä-Rajamäki et al. (Clin Oral Impl Res 2003, 14:158-165) indicated that increased levels of MMP-8 (collagenase-2) may be associated with the active phase of inflammatory peri-implant disease. The expression of MMP-9 (gelatinase B) has also been studied; while Ma et al. (Clin Oral Impl Res 2003, 14:709-713) showed an association between MMP-9 and bone levels, Aboyoussef et al. (Int J Oral Maxillofac Implants 1998, 13:689-696) failed to show any significant differences between healthy and peri-implantitis sites.

The imbalance between MMPs and tissue inhibitors of matrix metalloproteinases (TIMPs) is considered to trigger the degradation of extracellular matrix, basement membrane, and alveolar bone, and thus to initiate periodontal disease (Sorsa et al., Oral Diseases 2004, 10: 311-318). It has been suggested that salivary MMP-8, TIMP-1 and especially their ratios are potential candidates in the detection of advanced periodontitis (Gursoy et al., Clin Periodontol 2010, 37:487-493).

The plasminogen system is of central importance in extracellular proteolysis in physiological as well as pathological tissue remodeling (reviewed by Collen, Thromb Haemost 1999, 82:259-270). Plasmin is a broadly active protease that is capable of degrading many extracellular proteins as well as activating latent collagenase and other metalloproteinase (Werb et al., New Eng J Med 1977, 296:1017-1023; Matrisian, Bioessays 1992, 14:455-463). Plasmin acts directly on the extracellular matrix (ECM) by cleaving non-collagenous ECM proteins and also indirectly by activating proforms of a whole range of other enzymes, among them the matrix metalloproteinases (MMPs), with specificity for different connective tissue proteins. Through the interaction between the plasminogen system and other tissue degrading systems, plasminogen represents an important dormant proteolytic potential, and strict control of its activation is important for maintaining the integrity of the tissues. Plasmin is formed from its inactive precursor plasminogen by plasminogen activators (serine proteases of which two types have been identified: urokinase type, u-PA, and tissue type, t-PA), which are specifically inhibited by the plasminogen activator inhibitors (PAI-1 and PAI-2), through the formation of bimolecular 1:1 covalent complexes. The levels of tPA as well as PAI-2 have been shown to be higher in gingival crevicular fluid (GCF) from inflamed than healthy sites (Kinnby, Biol Chem 2002, 383:85-92). A relatively increased level of PAI-2 has been associated with tissue-protective functions in pregnancy as well as periodontitis (Kinnby et al., J Periodont Res 1996, 31:271-277; Olofsson et al., J Periodont Res 2002, 37:60-65).

Different treatment alternatives for peri-implant disease have been proposed. It has been suggested that non-surgical therapy (e.g. surface debridement without access surgery) may be successful in cases of peri-implant mucositis, but appears to be less effective for sites presenting peri-implantitis (Renvert et aL, J Clin Periodontol 2008, 35 (Suppl 8):305-315). Clinical data suggests that surgical treatment—e.g. open debridement including surface decontamination in combination with systemic antibiotics—may be a viable treatment option for peri-implantitis lesions (Claffey et al., J Clin Periodontol 2008, 35 (Suppl 8): 316-332). However, to date no common therapy exists, and advanced peri-implantitis remains difficult to treat. The marginal bone around the implant crestal region is usually a significant indicator of implant health. The level of the crestal bone may be measured from the crestal position of the implant at the initial implant surgery. The most common method to asses bone loss is by radiographic evaluation. The bone level can thus be measured on the radiographs and can be defined as the distance from the junction between the fixture and its abutment to the crest of the marginal bone mesially and distally to the implants (Ahlqvist et al., Int J Oral Maxillofac Implants 1990, 5(2):155-163). Of course, conventional radiographics only monitor the mesial or distal aspect of bone loss around the implant body (Misch et aL, Implant Dentistry 2008, 17(1):5-15). Lack of unambiguous information on ongoing bone loss may result in unnecessary or even incorrect treatment of peri-implant disease. The peri-implant bone level is determined from radiographs usually taken at the time of diagnosis The bone level is compared with what is considered normal, and one or more radiographs taken at earlier time points are used to assess the bone loss. However, radiographs provide a stationary image of the bone situation; hence, evidence of bone demineralization does not necessarily imply ongoing disease activity. This holds true also for periodontal bone levels, and data on progression of periodontitis do not demonstrate a continuous process but instead bursts of activity (exacerbation), remission and periods of inactivity (Hall et al., Eur J oral Implantol 2011, 4(4):371-382). In addition, the limited sensitivity of radiographs seldom allow for detection of the very early stages of the pathological bone degradation processes involved in several diseases. Moreover, it is important that all radiographic examinations be performed using appropriate and reproducible projection techniques. The precision in measurements performed on radiographs is low, especially when related to small average bone loss, and it indicates the difficulties involved in the interpretation of them. Furthermore, the bone loss rate can only be measured within a long period of time, typically one year (Ahlqvist et al., Int J Oral Maxillofac Implants 1990, 5(2):155-163), and involves exposing patients to frequent radiation. Therefore, it seems likely that establishment of ongoing bone degradation in peri-implantitis and periodontitis patients is a prerequisite for increased accuracy of individualized patient treatment.

Implant success allow for a rate of bone loss not exceeding 1.5 mm first year of implant loading and 0.2 mm/year thereafter. A higher progressive bone loss is indicative of peri-implantitis, implant overload or suboptimal implant placement hampering the healing capability at the implant site. Peri-implantitis and periodontitis progresses in a biphasic manner, where an active phase with bone loss is followed by a passive phase with no or insignificant bone loss and so on (Hall et al., Eur J oral Implantol 2011, 4(4):371-382). Therefore, if the bone loss rate should remain constant at a certain level, it will take a certain time before the implant or the tooth no longer is supported by anchoring bone, which depends on the length of the implant or tooth and the load bearing capability of the remaining surrounding bone.

SUMMARY OF THE INVENTION

Since lack of unambiguous information on ongoing bone loss may result in unnecessary or even incorrect treatment of conditions that affect bone, it is highly desirable to quickly and precisely establish the bone loss rate for increased accuracy of individualized patient treatment and disease prognosis. In the context of the present invention, bone loss rate may be defined as a measurement of the ongoing bone degradation. In other words, the bone loss rate may be defined as the variation of the bone level over time using the present invention. More preferably the invention manages to link the expression levels to variation of marginal bone level in the oral cavity, which profoundly help to guide the clinician in planning and providing relevant treatment. The limited sensitivity of radiographs seldom allow for detection of the very early stages of the pathological bone degradation processes involved in these diseases. Obtained radiographs provide information on marginal bone levels at the time of examination, but they do not provide unambiguous establishment of ongoing bone degradation. Moreover, the limit of quantification for measurements of marginal bone level changes using conventional radiographs has previously been estimated to 0.47 mm (Ahlqvist et al., Int J Oral Maxillofac Implants 1990, 5(2):155-163). Therefore, it seems likely that a quick establishment of ongoing bone degradation in patients suffering from a condition that affects bone is a prerequisite for increased accuracy of patient diagnosis and treatment. This also avoids exposure of patients to frequent radiation.

The present invention thus provides for a method for measuring the bone loss rate, wherein the method comprises the steps of:

a) quantifying the expression level of one or more markers or ratio thereof related to the activity of osteoclasts and/or osteoblasts in an ex vivo sample; and b) determining the bone loss rate as a function of ongoing loss of marginal bone level by interpolating the value obtained in step a) in one or more calibration curves.

Moreover, the present invention provides a kit for carrying out the methods of the invention. The present invention provides for a method and a kit that enables a clinician to more quickly and accurately provide unambiguous data of potential establishment of ongoing degradation. It means less exposure to radiographic devices and manages to link test result to a variation in bone level.

TERMS AND ABBREVIATIONS

CatK Cathepsin K
cDNA Complementary DNA
Cq Quantification cycle
DKK-1 Dickkopf-related protein-1
DNA Deoxyribonucleic acid
ECM Extracellular matrix
ELISA Enzyme Linked Immunosorbent Assay
GAPDH Glyceraldehyde-3-phosphate dehydrogenase
GCF Gingival crevicular fluid
HPRT1 Hypoxanthine-guanine phosphoribosyltransferase
IL Interleukin
MC Mucositis
MMPs Matrix metalloproteinases
mRNA Messenger RNA
OC Osteocalcin
OPG Osteoprotegerin
PAI-2 Plasminogen activator inhibitor type 2 (SerpinB2)
PI Peri-implantitis
PICF Peri-implant crevicular fluid
qPCR Quantitative Polymerase Chain Reaction
RANKL Receptor activator of NF-κB ligand
RNA Ribonucleic acid
SEQ Sequence
TIMPs Tissue inhibitors of matrix metalloproteinases
tPA Tissue plasminogen activator
TRAP Tartrate-resistant acid phosphatase
UBC Ubiquitin C
uPA Urokinase plasminogen activator
YWHAZ Tyrosine 3/tryptophan 5-monooxygenase activation protein, zeta polypeptide

DETAILED DESCRIPTION OF THE INVENTION

Figure 1:
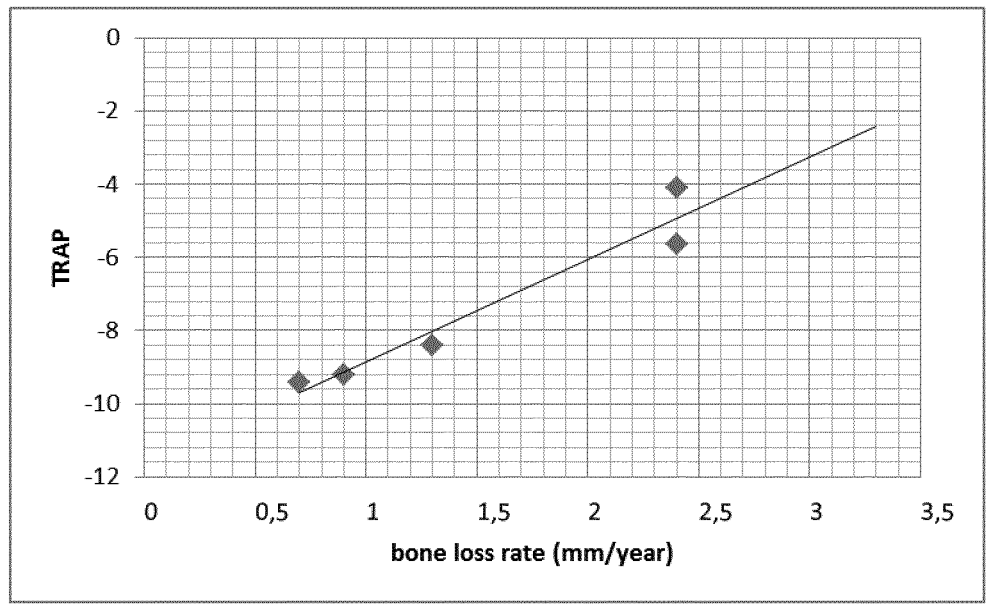
FIG. 1: Correlation between TRAP and bone loss rate. The bone degradation rate is represented in the X-axis (mm/year). The Y-axis represents the levels of TRAP (normalized expression).

The detailed description discloses specific and/or preferred variants of the individual features of the invention. The present invention also contemplates as particularly preferred embodiments those embodiments, which are generated by combining two or more of the specific and/or preferred variants described for two or more of the features of the present invention.

The present invention provides a method for measuring the bone loss rate. The method comprises the steps of (i) quantifying the expression level of one or more markers related to the activity of osteoclasts and/or osteoblasts or ratio thereof in an ex vivo sample and (ii) determining the bone loss rate by interpolating the value obtained in step (i) in one or more calibration curves. The inventors have shown that the levels of one or more markers related to the activity of osteoclasts and/or osteoblasts or a ratio between two or more of them are related to the bone loss rate. This allows for a quick and sensitive determination of the bone loss rate, which was not possible to perform before this invention. The bone loss rate can be indicative of the presence or absence of a condition that affects bone. Furthermore, the bone loss rate can indicate that the patient should undergo a certain treatment.

The term "interpolation in one or more calibration curves" is used herein with the meaning of estimating a value between the values already known or determined.

An implant can only be judged as osseointegrated in the context of a continuum of observation, since undermining interfacial changes may be gradual and not evident at the radiographic resolution level at least in the short term (Albrektsson et al., JOMI 1986, 1(1):11-25). The present invention provides a method for a quick detection of the bone loss rate, preventing the patient from undergoing unnecessary radiation exposure and providing the clinician with valuable information in order to diagnose, select the suitable therapy and/or estimate the prognosis of the implant.

In the context of the present invention, bone loss rate may be defined as a measurement of the ongoing bone degradation. In other words, the bone loss rate may be defined as the variation of the bone level over time. Time intervals are suitably chosen to detect specific phases after intervention, such as a healing phase, a loading phase, a post surgery phase the effect of surgery and/or the effect of the intervention in combination with a disease. It could for instance be of interest to follow up patients who are smokers or have diabetes or in other ways in a category with an exposure to the risk of bone loss. In the particular case of osseointegrated dental implants, the bone level may be defined as the distance from the junction between the fixture and its abutment to the crest of the marginal bone mesially and distally to the implant.

The ex vivo sample is preferably a body fluid or a tissue. The body fluid can be an oral fluid, and/or serum, and/or plasma, and/or cerebrospinal fluid, and/or synovial fluid, and/or peritoneal fluid, and/or blood, and/or saliva, preferably gingival crevicular fluid and more preferably peri-implant crevicular fluid.

The tissue can be bone, and/or a tissue adjacent to the bone, and/or connective tissue, and/or medulla, and/or cartilage, and/or gingiva, and/or mucosa, and/or implant-supporting tissue, and/or bone adjacent to an implant, and/or bone adjacent to a tooth.

The ex vivo sample in which the bone loss rate is measured may be obtained from the body fluid or tissue of the subject. Preferably, the ex vivo sample is obtained by inserting one or more sterile absorbents such as sterile paper points to the base of the peri-implant sulcus/pocket an left in situ for at least 60 seconds. Preferably, three or more sterile paper points are inserted in the sulcus/pocket.

Biomarkers (markers hereafter) may be defined as substances that are measured objectively and evaluated as an indicator of normal biologic processes, pathogenic processes and pharmacologic responses to a therapeutic intervention. Biomarkers are molecules that may be used to monitor health status, disease onset, treatment response and outcome (Zia et al., Biology and medicine 2011, 3(2):45-52).

Markers related to the activity of osteoclasts and/or osteoblasts are markers related to bone metabolism (bone turnover and/or bone formation and/or bone resorption and/or bone remodeling) and are well known in the art (i.e. Hall et al., Eur J Oral Implantol 2011, 4(4):371-382; Seibel, Clin Biochem Rev 2005, 26:97-122; Watts, Clin Chem 1999, 45(8)B:1359-1368; Christenson, Clin Biochem 1997, 30(8):573-593).

The marker or combination thereof, or ratio thereof related to the activity of osteoclasts and/or osteoblasts is not particularly limited and may be one or more of TRAP, and/or OPG, and/or CatK, and/or RANK, and/or RANKL, and/or osteocalcin, and/or IL-6, and/or DKK-1, and/or MMP-8, and/or MMP-2, and/or TIMP-1, and/or tPA, and/or PAI-2, and/or other markers from the Cathepsin family, and/or bone sialoprotein (BSP), and/or alkaline phosphatase (ALP) and/or markers from the TGF-β superfamily such as bone morphogentic proteins (BMPs), and/or macrophage colony stimulating factor (M-CSF), and/or sclerostin (protein product from the Sost (Sclerosteosis gene)), and/or Noggin or combinations thereof. Preferred are those markers or ratio of markers that provide a linear relationship between the expression levels of those markers or ratio of markers and the bone loss rate, such as TRAP, and/or OPG, and/or CatK and/or osteocalcin, and/or TRAP/OC, and/or Catk/OC. Alternatively, preferred are those markers or ratio of markers that provide a quadratic, and/or a cubic relationship, and/or quartic relationship, and/or quantic relationship, and/or exponential relationship, and/or logarithmic relationship between the expression levels of those markers or ratio of markers and the bone loss rate.

The markers of the present invention may be identified by the following accession numbers:
Interleukin-1 beta (IL-1 b): NM_000576.2
Interleukin-6 (IL-6): NM_000600.3
Matrix metalloproteinase-8 (MMP8): NM_002424.2
Tartrate resistant acid phosphate (TRAP): NM_001611.3
Cathepsin K: NM_000396
Osteoprotegerin (OPG): NM_002546
Receptor activator of the NF-kB ligand (RANKL): NM_003701.3
Interleukin-8 (IL8): NM_000584.3
Homo sapiens dickkopf 1 homolog (*Xenopus laevis*) (DKK1): NM_012242.2
Tissue inhibitor of matrix metalloproteinase (TIMP-1): NM_003254.2
Tissue plasminogen activator (TPA): NM_000930.3
Plasminogen activator inhibitor type 2 (serpinB2) (PAI-2): NM_001143818.1
Osteocalcin (PMF1 or OC): NM_001199654.1

Preferably, the expression level of two, three, four, five, six or more markers or ratio thereof is measured in order to obtain more accurate information on bone loss rate.

Dickkopf-related protein-1 (DKK-1) is a Wnt signaling antagonist, and it reduces osteoblast differentiation. Elevated systemic levels of DKK-1 have been measured in subjects with rheumatoid (Liu et al., Chin Med J (Engl). 2010, 123(11):1407-12) and psoriatic arthritis (Dalbeth et al., Arthritis Res Ther. 2010, 12(4):R164).

Tartrate-resistant acid phosphatase (TRAP) is secreted from the osteoclast ruffled border, dephosphorylates osteopontin that act as an anchor to osteoclasts before dephosphorylation, and allows osteoclast migration and further bone resorption (Minkin, Calcif Tissue Int, 1982, 34:285-290).

The method for quantifying the expression level of one or more markers or ratio thereof related to the activity of osteoclasts and/or osteoblasts in the ex vivo sample is not particularly limited and may be selected from a method of quantifying nucleic acids such as mRNA and/or a method for quantifying proteins such as RT-qPCR, hereafter referred to as qPCR, and/or Northern Blot, and/or immunoassay, and/or ELISA, and/or radioimmunoassay, and/or magnetic immunoassay, and/or fluorescent immunoassay, and/or immunoprecipitation, and/or surface plasmon resonance, and/or Western Blot, and/or immunohistochemistry or any combination thereof. A preferred method for quantification is qPCR. Experimental procedures typically include sample-processing steps (i.e. extraction).

The quantification of the expression level of one or more markers or ratio thereof may be normalized by one or more reference genes. Normalization involves reporting the ratios of the expression level of the genes of interest to those of the reference genes. The reference genes can be selected using the freely available NormFinder17 program. Preferably, the reference genes are those which are stably expressed and their abundances show a strong correlation with the total amount of sample (in the case of qPCR, with the total amount of mRNA). More preferably, the reference genes are selected from GAPDH, YWHAZ, UBC and/or HPRT-1, among which YWHAZ and UBC are preferred.

The reference genes of the present invention may be identified by the following accession numbers:
YWHAZ (Reference gene): NM_001135702.1
UBC (Reference gene): NM_001135702.1

In the context of the present application, expression level of a marker may mean (i) concentration, or (ii) detection signal specific for a marker, or (iii) a value that relates to (i) and/or (ii) by mathematical transformation.

In the case of qPCR, relative gene expression levels are preferably calculated using the ΔΔCq method (Livak et al., Methods 2001, 25:402-408) for each assay and by normalizing gene expression of each gene by the reference genes. The reference genes may be for example selected using the freely available NormFinder program (www.mdl.dk/publicationsnormfinder.htm. October 2010). The normalized gene expression can then be calculated for each subject using the following expression after logarithmic transformation: normalized expression of gene g=(Cq(n)−Cq(g)), where Cq(g) is the number of amplification cycles for gene g, and Cq(n) is the normalization factor (mean number of amplification cycles for the selected reference gene or genes) for the sample taken from the subject.

In the case of qPCR, the expression level of one or more markers or ratio thereof related to the activity of osteoclasts and/or osteoblasts may be also quantified by quantification of the corresponding amplicon. An amplicon may be defined a piece of DNA or RNA that is the source and/or product of natural or artificial amplification or replication events. In the case of the present invention, the preferred amplicons for the quantification of the expression level of the one or more markers or ratio thereof related to the activity of osteoclasts and/or osteoblasts or reference genes are the following:
Interleukin-1 beta (IL-1 b): SEQ ID NO 1
Interleukin-6 (IL-6): SEQ ID NO 2
Matrix metalloproteinase-8 (MMP8 SEQ ID NO 3
Tartrate resistant acid phosphate (TRAP): SEQ ID NO 4
Cathepsin K: SEQ ID NO 5
Osteoprotegerin (OPG): SEQ ID NO 6
Receptor activator of the NF-kB ligand (RANKL): SEQ ID NO 7
Interleukin-8 (IL8): SEQ ID NO 8
*Homo sapiens* dickkopf 1 homolog (*Xenopus laevis*) (DKK1): SEQ ID NO 9
Tissue inhibitor of matrix metalloproteinase (TIMP-1): SEQ ID NO 10
Tissue plasminogen activator (TPA): SEQ ID NO 11
Plasminogen activator inhibitor type 2 (serpinB2) (PAI-2): SEQ ID NO 12
Osteocalcin (PMF1 or OC): SEQ ID NO 13
YWHAZ (Reference gene): SEQ ID NO 14
UBC (Reference gene): SEQ ID NO 15

In the methods of the present invention the one or more calibration curves may provide a linear relationship and/or a cubic relationship, and/or a quadratic relationship, and/or quartic relationship, and/or quantic relationship, and/or exponential relationship, and/or logarithmic relationship between the bone loss rate and the expression levels of marker or ratio of markers. Preferably, the calibration curve may provide a linear relationship between the bone loss rate and the expression levels of marker/ratio of markers. The calibration curve should be established using the same one or more markers and/or ratio thereof and the same quantification technique as used for the ex vivo sample to be interpolated in it.

The methods of the present invention may be used for indicating the presence or absence of a condition that affects bone, preferably of a condition that affects bone surrounding implants and/or teeth. More preferably, said condition is peri-implant disease, and/or periodontal disease, and/or arthritis, and/or rheumatoid arthritis, and/or psoriatic arthritis, and/or osteoporosis and/or a combination thereof, among which peri-implant disease is preferred.

Peri-implant disease (also called peri-implantitis in presence of bone degradation) is defined as an inflammatory process affecting the tissue around an implant in function that has resulted in loss of supporting bone (Becker et al., Int J Oral Maxillofac Implants 1990, 5:31-38). Mucositis is often referred to as soft tissue inflammation, swelling, bleeding on probing and in some cases, suppuration, but with no signs of bone loss.

The methods of the present invention may be also used for evaluation of the prognosis of an implant.

The present inventors investigated the association between the expression level of certain markers or ratio between two or more markers or combination thereof that are related to the activity of osteoclasts and/or osteoblasts and the bone loss rate, enabling the use as diagnostic factor for conditions that affect bone. Thus, by the method of the invention, an individual patient can be diagnosed to suffer or not to suffer from a condition that affects bone, preferably a condition that affects bone surrounding implants and/or teeth.

The inventors have shown that the expression level of certain markers or ratio between two or more markers that are related to the activity of osteoclasts and/or osteoblasts in peri-implant crevicular fluid obtained from patients that have undergone implant treatments is related to the bone loss rate. This method provides a quick determination of the bone loss rate, which is necessary in order to diagnose peri-implant disease and to select the appropriate treatment.

With the method of the present invention, it is possible to detect the bone loss rate due to overload resulting from poor prosthetic constructions, the bone loss rate due to placement of too large implants in narrow alveolar ridges, and other cases were implant placement has resulted in a too thin bone sections. Accordingly, the clinician would provide the appropriate treatment. It is thus not necessary to expose the subjects to radiation, and the clinician does not have to wait until the bone degradation has progressed to a measurable level assessed by radiographs to select a treatment and establish a prognosis of the patient.

The ex vivo sample in which the bone loss rate is measured may be obtained from a patient which may or may not suffer from a condition that affects bone, preferably from a condition that affects bone surrounding implants and/or teeth. The preferred patient is a patient with one or more implants, more preferably a bone anchored implant. The implant might be a dental implant, and/or a hip implant, and/or a knee implant.

Preferably, the patient suffers and/or is likely to suffer from a condition that affects implant supporting tissue, and/or a condition that affects bone supporting implants, and/or a condition that affects the tissues around teeth, such as peri-implantitis, and/or mucositis, and/or periodontitis, and/or gingivitis or a combination thereof. More preferably, said patient suffers and/or is likely to suffer from peri-implant disease. Alternatively, the patient suffers and/or is likely to suffer from a condition that affects bone, such as arthritis, rheumatoid arthritis, psoriatic arthritis, osteoporosis, and the like.

The expression levels of 1, 2, 3, 4, or 5 or 6 of TRAP, TRAP/OC, CatK/OC and OPG in an ex vivo sample of a patient may be quantified by qPCR. The determination of bone loss rate may be performed by interpolating one or more values obtained in the quantification step in a calibration curve. Preferably, this information is indicative of an appropriate treatment and/or disease prognosis.

A bone loss rate of or lower than 0.2 mm/year may be indicative of a treatment comprising standard of care oral hygiene treatment and a maintenance program.

A bone loss rate within the range of 1 to 1.5 mm/year may be indicative of a treatment comprising standard of care oral hygiene treatment and a maintenance program and a follow up visit within few months.

A bone loss rate of or higher than 2.0 mm/year may be indicative of a need for surgical treatment.

Bone loss rate not exceeding 1.5 mm/year during the first year after implantation or less than 0.2 mm/year thereafter might be indicative of a standard program for oral hygiene.

Bone loss rate of 0.2 to 2.0 mm/year after the first year of implant insertion might be indicative of a standard program for oral hygiene and a follow up visit within a few months. If the bone loss rate remains 1.5 to 2.0 mm/year, the clinician might perform surgical treatment of the site.

Bone loss rate of more than 1.5 mm/year during the first year after implant insertion might be indicative of incorrect implant position or inefficient implant loading and may be indicative of surgical treatment. High bone loss rate of more than 2.0 mm/year after the first year of implant insertion might be indicative of surgical treatment.

The terms "human subject", "subject" and "patient" are used interchangeably in the application. The terms "condition" and "disease" are used interchangeably in the application.

Further, the present invention provides a kit for carrying out the methods of the invention. The bone loss rate value indicative for a certain treatment may be provided with the kit. With the help of the kit, the bone loss rate of a patient can be calculated. The kit of the invention might comprise a sample collection device, which is not limited and is a device for taking samples such as body fluids or tissue. Preferably, the sample collecting device is used for taking samples of peri-implant crevicular fluid. The sample collection device may be absorbents such as sterile paper points and/or a syringe and/or a biopsy device. Preferably, the sample collection devices are sterile absorbents, more preferably sterile paper points.

The kit of the present invention may further comprise a preservation medium for preserving the sample. The purpose of the preservation medium is to preserve biological samples, and may be any medium formulated to maintain the integrity and viability of the samples for downstream analysis. Preferably, the preservation medium may comprise inhibitors of RNases. Most preferably, the preservation medium is RNALater preservation medium (Qiagen, Hilden, Germany).

The kit of the present invention may also contain instructions on how to perform the method of the invention.

The kit of the present invention may further contain a box to send the sample to a central laboratory, where the expression levels of one or more markers related to the activity of osteoclasts and/or osteoblasts or combination thereof are quantified. The interpolation of the expression level value in one or more calibration curves may be performed in the central laboratory. Alternatively, the kit may contain one or more calibration curves where the expression level value may be interpolated and correlated to the bone loss rate.

Alternatively, the kit of the present invention may contain the necessary elements to quantify the expression levels of one or more markers related to the activity of osteoclasts and/or osteoblasts or combination thereof. In this case, the kit may comprise at least one detectable label and at least one substrate which specifically recognizes one or more markers related to the activity of osteoclasts and/or osteoblasts or combination thereof.

If the quantification is performed by means of mRNA quantification, said kit may also comprise one or more primer sequences in order to detect and quantify the markers related to the activity of osteoclasts and/or osteoblasts.

If the quantification is performed by means of protein quantification, said kit may also comprise one or more substrates to detect and quantify the markers related to the activity of osteoclasts and/or osteoblasts. Preferred substrates are antibodies, either monoclonal, polyclonal or fragments thereof. The kit may further comprise primary and secondary antibodies, and labeled antibodies.

In these cases, the kit may also comprise one or more calibration curves in order to interpolate the expression level value and determine the bone loss rate.

The kit may be used and the use is not particularly limited, although use in the method of the invention in any of its embodiments is preferred.

"One or more" also as used herein includes one and the individualized specification of any number which is more than one, such as two, three, four, five, six, etc. "More than one" or "several" as used herein includes the individualized specification of any number which is more than one, such as two, three, four, five, six, etc.

Unless expressly specified otherwise, the term "comprising" is used in the context of this document to indicate that further members may optionally be present in addition to the members of the list introduced by "comprising". It is, however, contemplated as a specific embodiment of the present invention that the term "comprising" encompasses the possibility of no further members being present, i.e. for the purpose of this embodiment "comprising" is to be understood as having the meaning of "consisting of".

EXAMPLES

Example 1: Calibration Curve

Subjects

This was a non-randomised, single-blinded (sample analysts) controlled clinical exploratory study which was approved by the local ethical committee, University of Göteborg, Sweden (Dnr: 652-10). The study included 25 subjects with healthy implant sites, 25 subjects with sites with peri-implant mucositis and 25 subjects with obvious clinical signs of peri-implantitis. The study was limited to a single evaluation time point. Study participants were selected from subjects previously rehabilitated with dental implants attending scheduled implant maintenance sessions at the Brånemark Clinic, Göteborg, Sweden. Each subject participated in the informed consent process and signed and dated the informed consent form (ICF) before any study related procedures were performed. One implant site per subject was evaluated, and the selected site was categorized as a healthy (HI), mucositis (MC) or peri-implantitis (PI) site on the basis of criteria described below. Peri-implant crevicular fluid (PICF) was collected from the implant sites using three pooled paper points per site. All persons involved in sample analysis and statistics were blinded to subject identity, and persons involved in sample analysis were also blinded to sample type (HI, MC or PI). Analysis of the expression of genetic markers was performed by an independent test laboratory (Tataa Biocenter, Göteborg, Sweden).

Inclusion/Exclusion Criteria

For participation in the present study each subject fulfilled each of the general criteria 1-5 provided in Table 1. In order to be included in either the HI, MC or PI group, the subjects had to fulfill the inclusion criteria provided in Table 2, 3 and 4, respectively. The exclusion criteria for all three groups are provided in Table 5. Subject health conditions and treatments such as anti-inflammatory treatment, osteoporosis, diabetes, uncontrolled hyperparathyroidism, corticosteroid and bone anabolic therapies, history of malignancy, use of tobacco and/or other nicotine containing products were not exclusion criteria, but such conditions, treatments and use were recorded in the Case Report Forms (CRFs). All regular prescription medication and/or other regular treatment received within 30 days before subject enrolment, except anti-biotic treatment, was permitted and recorded in the CRFs. Antibiotic treatment within 3 months prior to study enrolment was prohibited.

Subject age, gender, oral health, Mombelli modified Bleeding Index (mBl), modified Plaque Index (mPl), Peri-Implant Pocket Depth (PIPD), height of attached mucosa and presence of suppuration was also recorded and quantified in the CRFs for all subjects.

Subject enrolment in both groups was performed in a consecutive manner provided the subjects fulfilled the eligibility criteria. The inclusion period was approximately one year, where subjects in all three groups were enrolled during the entire period.

Randomization was not applicable. The clinical investigator performing the clinical examination and PICF sampling was not blinded to the study parameters. All other persons involved in sample analyses were blinded to subject identity. The persons involved in performing qPCR analysis of PICF samples were blinded to the type of sample (HI, MC or PI). Persons involved in performing statistical analyses were not blinded to the study populations.

Collection of Samples

The PICF sampling was performed as follows: Three sterile paper points (Roeke, Coltene, Germany) were inserted to the base of the peri-implant sulcus/pocket and left in situ for at least 60 seconds at the selected implant site. The three paper points were immediately transferred to one (1) 2 ml plastic tube (Microtube, 2 ml, Sarstedt, Numbrecht, Germany) containing RNALater preservation medium (Qiagen, Hilden, Germany); i.e. the three samples were pooled. Clean gloves were always used when handling the tubes. The paper points were completely immerged in the preservation medium. The pooled sample was transferred from the Branemark Clinic the sampling day at ambient temperature to the local lab for analysis of gene markers.

Handling and Analyses of Samples

Analysis of the qPCR samples were performed by TATAA Biocenter AB (Göteborg, Sweden) as per standard procedures, which has been previously described in Hall et al. (Eur J Oral Implant 2011, 4(4):371-382). In brief, RNA from cells attached to the paper points were extracted at TATAA Biocenter. The cells were then purified using Qiagen RNeasy Micro kit (Qiagen AB, Solna, Sweden) according to the manufacturer's instructions. Carrier RNA included in the kit was used to minimize losses of RNA during extraction. RNA was converted to cDNA using BioRad iScript cDNA synthesis kit (Bio-Rad Laboratories Inc., Hercules, Calif., USA) according to the manufacturer's instructions using 5 µl of the RNA. The cDNA was diluted to 50 µl in UltraPure water (Invitrogen Corp., Carlsbad, Calif., USA). Quantitative polymerase chain reaction (qPCR) assays of the samples were then performed. The analyzed biochemical markers are listed in the table 6. Perfecta SYBR Green Supermix (Quanta BioSciences, Gaithersburg, Md., USA) and 2 µl of cDNA template together with 0.4 µM of forward and reverse primer were used in the quantitative PCR. Each cDNA sample was quantified in duplicate. The following temperature protocol was employed: enzyme activation 3 min at 98° C. followed by 45 cycles of 20 seconds at 95° C., 20 seconds at 60° C. and 20 seconds at 72° C. Fluorescence detection was performed in a FAM/SYBR channel during the last temperature cycle. Experiments were performed on the LightCycler 480 System (Roche, Penzberg, Germany). After amplification a dissociation/melting curve was generated to verify that specific products were generated. Relative gene expression levels were calculated using the $\mathbb{I} Cq$ method (Livak et al., Methods 2001, 25:402-408) using 90% efficiency for each assay and by normalizing gene expression of each gene by two reference genes (UBC and YWHAZ) that were selected using the freely available NormFinder17 program. The two genes were selected after running four genes, GAPDH, YWHAZ; UBC, HPRT-1, in the program. The selection of the four normalization genes was based on the results from our previous feasibility study (Hall et al., Eur J oral Implantol 2011, 4(4):371-382), where 9 reference genes were investigated and PICF sampling using paper points was also used. The main criterion was that the variation in reference gene expression should be minimal within and between the HI, MC and PI groups.

Limit Of Quantification (LOQ) was determined for Cq for all genes based on purified PCR product quantified by spectrophotometer. A five-point standard curve with four replicates in each point was generated for all assays, and run in ten-fold dilution series in concentrations between 10 and $10^6$ copies/µl. All data above the determined LOQ-values was omitted from the analyses. The procedure resulted in reduction of data scattering and narrowing of the data distributions, which increased the possibility for observation of significant differences in gene expression between the three subject groups.

In order to investigate if the qPCR analysis was inhibited by the sample matrix, e.g. presence of suppuration, 14 of the samples from the PI group were spiked with a known concentration of RNA-spike (#RS12JG, TATAA Biocenter AB) and compared by water samples spiked with the same concentration. One sample was taken with a sterile aspiration needle from one implant site exhibiting suppuration from the 14 subjects in the PI group. The aspiration needle sampling site was not the same but similar to the paper point sampling site. The aspiration needle (Metal Suction Tip, 0.7×70 mm 22G, Mediplast, Malmö, Sweden) was inserted to the base of the peri-implant sulcus/pocket at the selected site. The needle containing the sample was immediately removed from the plastic syringe (1 ml, BD Plastipak, Mediplast, Malmö, Sweden) bent gently and put into one (1) 4.5 ml plastic cryo tube (Nunc CryoTube Vials, Fisher Scientific, Göteborg, Sweden). The lid of the tube was closed, and the tube was positioned and frozen at $-196°$ C. in a thermos with liquid nitrogen and transported immediately to the lab (TATAA Biocenter) for inhibition analysis. Clean gloves were always used when handling the aspiration needles and the plastic tubes.

Statistical Methods

Differences in gene marker expression between the three study groups were estimated using analysis of variance (ANOVA). In the analysis of data, logarithmic data transformation was performed and ninety-five percent (95%) confidence intervals for differences between independent samples were used.

The normalized gene expression was calculated for each subject using the following expression after logarithmic transformation: normalized expression of gene $g=(Cq(n)-Cq(g))$ where $Cq(g)$ is the number of amplification cycles for gene g, and $Cq(n)$ is the normalization factor (mean number of amplification cycles for the selected reference genes) for the sample taken from the subject. The analysis of variances was performed using the normalized expression of gene g in the HI, MC and PI groups.

A p-value less than 0.05 would have been considered statistically significant if the investigation of possible differences between the HI, MC and PI groups comprised only two genetic markers. However, since the study comprised 8 markers after some had been excluded during the LOQ analysis, the Bonferroni correction for mass significance was used, and a p-value less than 0.0063 was considered statistically significant.

The calculated normalized gene expression for each subject was then correlated to the information on bone loss provided by the radiographs of that same subject at the same time point. Radiographic examination techniques are well known in the field and can be performed as described in Ahlqvist et al. (Int J Oral Maxillofac Implants 1990, 5(2): 155-163). The bone level can be measured on the radiographs and it is defined as the distance from the junction between the fixture and its abutment to the crest of the marginal bone mesially and distally to the implants.

TABLE 1

General Inclusion Criteria given informed consent to participate in the study
18 years or older
rehabilitated with dental implant in the maxilla and/or mandible.
The implants should have been in function for more than 1 year
conditions that allow for collection of PICF using periodontal paper points and aspiration needles
at least two evaluable radiographs of the three implants taken at two different time points after at least 1 year in function must be available. The most recent radiographs shall not be older than 3 months

TABLE 2

Inclusion Criteria for Subjects in the HI group no radiographic evidence of pathologic bone loss (rate of bone loss not exceeding 1.5 mm first year of implant loading and 0.2 mm/year thereafter) around any of the implants
no signs of inflammation and no/limited bleeding on superficial probing around any of the implants (modified bleeding index, mBI = 0 or 1)
no suppuration on palpation at any of the implants

TABLE 3

Inclusion Criteria for Subjects in the MC group no radiographic evidence of pathologic bone loss (rate of bone loss not exceeding 1.5 mm first year of implant loading and 0.2 mm/year thereafter) at any of the implant sites
bleeding on superficial probing around at least three implants (modified bleeding index, mBI = 2 or 3)
redness and swelling of the peri-implant mucosa around implants presenting bleeding on superficial probing

TABLE 4

Inclusion criteria for subjects in the PI group at least three implant sites with radiographs showing obvious signs of pathologic bone loss
bleeding on superficial probing around at least three implants (modified bleeding index, mBI = 2 or 3)
suppuration upon palpation around implants presenting radiographic bone loss and bleeding on superficial probing

TABLE 5

Exclusion Criteria not able to give his/her informed consent to participate in the study
history of antibiotic treatment within 3 months prior to study inclusion
has had augmentation procedures performed at any of the selected implant sites
has implant supported overdenture in the jaw of interest

TABLE 6

Analysed gene markers

| # | Gene marker | SEQ ID NO | Abbreviation | Main biological process |
|---|---|---|---|---|
| 1 | Osteocalcin | 13 | OC | Bone formation |
| 2 | Tartrate resistant acid phosphatase | 4 | TRAP | Bone remodeling |
| 3 | Cathepsin K | 5 | CatK | Bone resorption |
| 4 | Osteoprotegerin | 6 | OPG | Bone remodeling |
| 5 | Interleukin 6 | 2 | IL-6 | Bone degradation |
| 6 | Tyrosine 3/tryptophan 5-monoxygenase activation protein, zeta polypeptide | 14 | YWHAZ | Normalisation gene |
| 7 | Ubiquitin C | 15 | UBC | Normalisation gene |

TABLE 7

Soft tissue status

|  | HI Group | MC Group | PI Group |
|---|---|---|---|
| mBI | 0.2 (SD = 0.4) | 1.6 (SD = 0.5) | 2.3 (SD = 0.6) |
| mPI | 0.04 (SD = 0.14) | 0.8 (SD = 0.9) | 0.6 (SD = 1.0) |
| PIPD (mm) | 2.1 (SD = 0.7) | 3.1 (SD = 0.9) | 5.5 (SD = 2.3) |
| Height of attached mucosa (mm) | 1.3 (SD = 1.0) | 1.4 (SD = 1.1) | 1.3 (SD 1.2) |
| Suppuration (#subjects) | 0 | 7 | 25 |

TABLE 8

Number of subjects with main compromised health conditions

|  | HI | MC | PI |
|---|---|---|---|
| History of periodontitis | 3 | 9 | 11 |
| History of peri-implantitis | 0 | 3 | 14 |
| Smoker | 1 | 10 | 14 |
| Poor oral hygiene | 0 | 13 | 12 |
| High blood pressure | 7 | 8 | 8 |
| Cardiovascular disease | 4 | 6 | 6 |
| High cholesterol | 2 | 2 | 4 |
| Allergy | 4 | 4 | 5 |

Example 2

Levels of TRAP are quantified in peri-implant crevicular fluid obtained from a patient that has undergone implant treatments. Expression levels of TRAP are quantified by qPCR as described in example 1. The value obtained is then interpolated in a calibration curve (i.e. FIG. 1) and the bone loss rate of said patient is estimated.

Example 3

Figure 2:
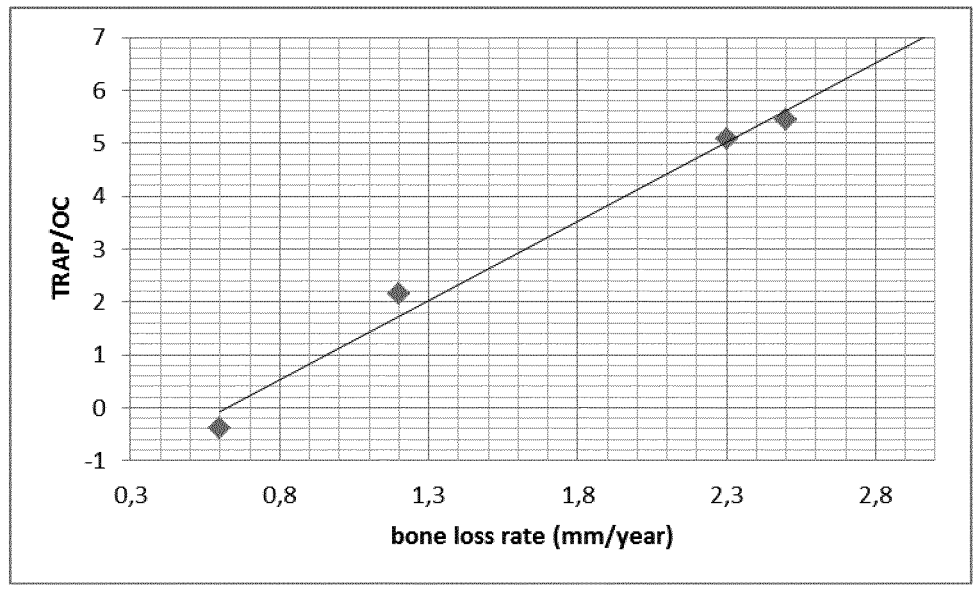
FIG. 2: Correlation between TRAP/OC and bone loss rate. The bone degradation rate is represented in the X-axis (mm/year). The Y-axis represents the levels of TRAP/OC (normalized expression).

Expression levels of TRAP and expression levels of OC are quantified in peri-implant crevicular fluid obtained from a patient that has undergone implant treatments. Expression levels of TRAP and OC are quantified by qPCR as described in example 1. The ratio of the values obtained (TRAP/OC) is then interpolated in a calibration curve (i.e. FIG. 2), and the bone loss rate of said patient is estimated.

Example 4

Figure 3:
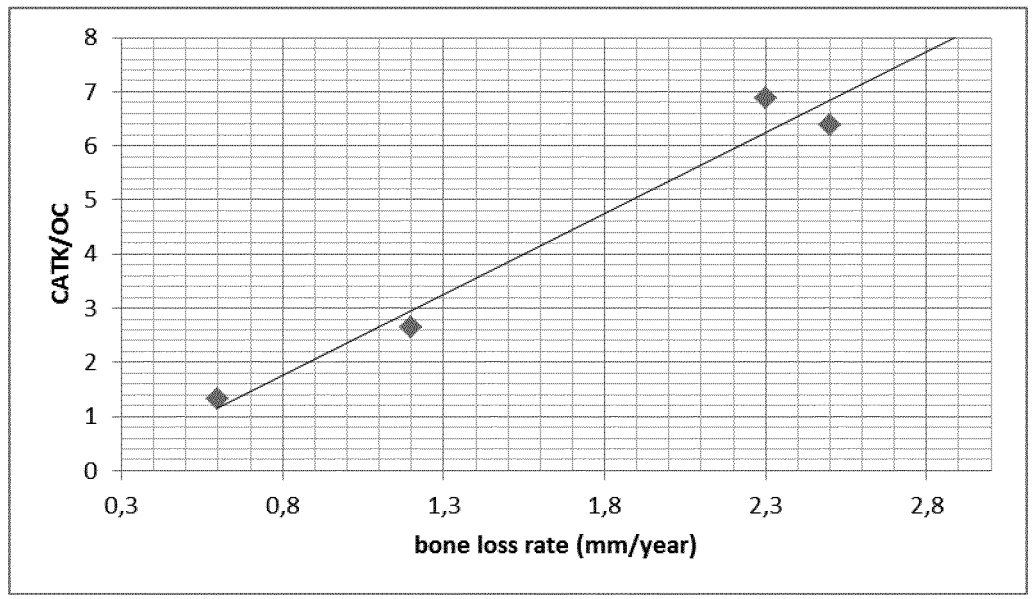
FIG. 3: Correlation between CatK/OC and bone loss rate. The bone degradation rate is represented in the X-axis (mm/year). The Y-axis represents the levels of CatK/OC (normalized expression).

Levels of CatK and OC are quantified in peri-implant crevicular fluid obtained from a patient that has undergone implant treatments. Expression levels of CatK and OC are quantified by qPCR as described in example 1. The ratio of the values obtained (CatK/OC) is then interpolated in a calibration curve (i.e. FIG. 3), and the bone loss rate of said patient is estimated.

Example 5

Figure 4:
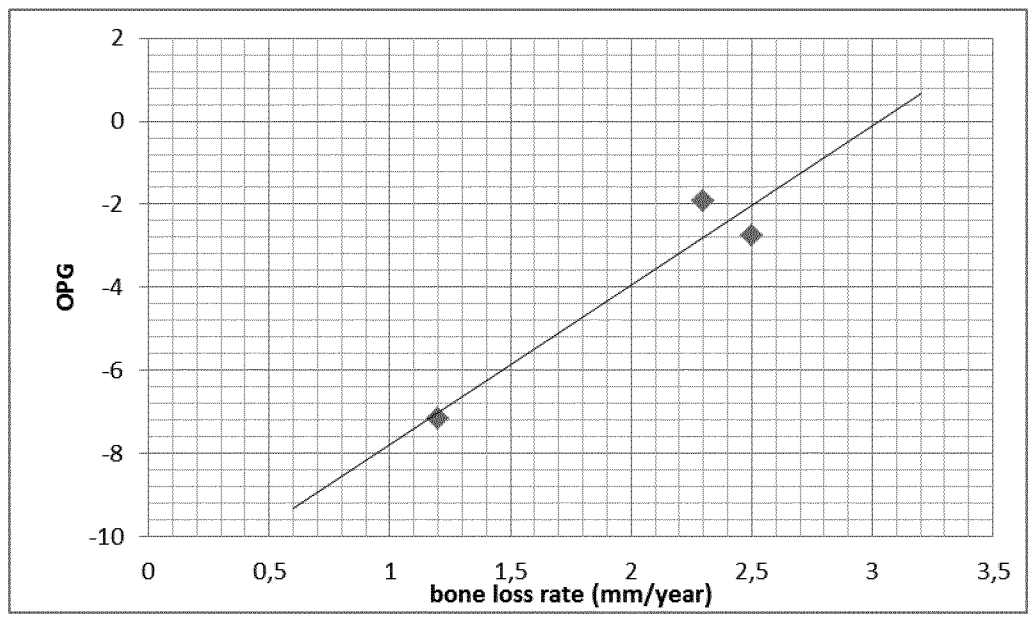
FIG. 4: Correlation between OPG and bone loss rate. The bone degradation rate is represented in the X-axis (mm/year). The Y-axis represents the levels of OPG (normalized expression).

Levels of OPG are quantified in peri-implant crevicular fluid obtained from a patient that has undergone implant treatments. Expression levels of OPG are quantified by qPCR as described in example 1. The value obtained is then interpolated in a calibration curve (i.e. FIG. 4), and the bone loss rate of said patient is estimated.

Example 6

In one or more of the Examples 2-5, a patient may show soft tissue inflammation and a bone loss rate up to 0.2 mm/year. In this case, the clinician may provide the subject with a standard program of care oral hygiene treatment. A follow up visit may be scheduled within several months or a year.

Example 7

In one or more of the Examples 2-5, the clinician concludes that rapid and extensive bone degradation is likely ongoing (bone loss rate>2 mm/year), provide the subject with oral hygiene treatment and schedule a follow up visit within a few months. If the bone loss rate remains >2 mm/year at the second follow up visit, the clinician may decide to perform surgical treatment of the site.

Example 8

In one or more of the Examples 2-5, a subject exhibits obvious signs of peri-implantitis, i.e. peri-implant inflammation, swelling, redness, suppuration and pathologic, crater shaped marginal bone loss. However, the bone loss rate was <0.2 mm/year, and the clinician concluded that surgical treatment was unnecessary and provided the subject with oral hygiene treatment, maintenance protocol and scheduled a follow up visit within a few months.

Example 9

In another example, a sample taken from a subject exhibiting inflammation and bleeding on probing shows that the TRAP/OC ratio corresponds to a bone loss rate between 0.2 and 0.5 mm/year. The clinician concludes that bone degradation is likely very low and insignificant, and provides the subject with standard of care oral hygiene program. A follow up visit is scheduled within several months or a year.

Example 10

In a further example, a sample taken from another subject exhibiting similar clinical signs of mucositis has a TRAP/OC ratio that corresponds to a bone loss rate exceeding 2 mm/year. The clinician concludes that rapid and extensive bone degradation is likely ongoing, provides the subject with oral hygiene treatment and schedule a follow up visit within a few months. If the TRAP/OC ratio remains high at the second follow up visit, the clinician decides to perform surgical treatment of the site.

Example 11

In another example, a subject exhibits obvious signs of periimplantitis, i.e. periimplant inflammation, swelling, redness, suppuration and pathologic, crater shaped marginal bone loss. However, the TRAP/OC ratio corresponds to a bone loss rate less than 0.5 mm/year, and the clinician concludes that surgical treatment is unnecessary and provides the subject with oral hygiene treatment protocol and schedules a follow up visit within a few months.

It was not necessary to expose the subjects of examples 9 to 11 to radiation, and the clinician did not have to wait until the bone degradation had progressed to a measurable level assessed by radiographs in the two latter examples.

The invention claimed is:

1. A method of measuring bone loss rate and treating periodontal or peri-implant disease in a subject, wherein the method comprises the steps of:
    a) obtaining a value of an expression level of one or more markers or ratio thereof related to activity of at least one of osteoclasts or osteoblasts in an ex vivo gingival or peri-implant crevicular fluid sample obtained from a subject to determine if the subject has periodontal or peri-implant disease,
       wherein the one or more markers or ratio thereof comprises a marker or ratio thereof selected from the group consisting of tartrate-resistant acid phosphatase (TRAP), TRAP/osteocalcin ratio, CatK/osteocalcin ratio, and osteoprotegerin (OPG);
    b) determining the bone loss rate of the subject as a function of ongoing loss of marginal bone level by interpolating the value obtained in step a) in one or more calibration curves; and
    c) treating the subject based on the determined bone loss rate of the subject, the treatment comprising a surgical treatment when the determined bone loss rate is higher than 2.0 mm/year.

2. The method according to claim 1, wherein said value is obtained by nucleic acid quantification.

3. The method according to claim 2, wherein said quantification is performed by at least one of qPCR or Northern Blot.

4. The method according to claim 1, wherein said one or more calibration curves provide a linear relationship, a quadratic relationship, a cubic relationship, quartic relationship, quantic relationship, exponential relationship, or logarithmic relationship between the bone loss rate and the expression level of one of more markers or ratio of markers or combinations thereof.

5. The method according to claim 4, wherein said one or more calibration curves provides a linear relationship between the bone loss rate and the expression level of one or more markers or ratio of markers or combinations thereof.

6. The method according to claim 1, wherein said subject is treated for peri-implant disease.

7. The method according to claim 1, wherein said subject is treated for periodontal disease.

8. The method according to claim 1, wherein the treatment comprises oral hygiene treatment and a maintenance program when the determined bone loss rate is 0.2 mm/year or lower.

9. The method according to claim 1, wherein the treatment comprises oral hygiene treatment, a maintenance program and a follow up visit when the determined bone loss rate is within the range of 1 to 1.5 mm/year.

* * * * *